United States Patent
Ohhira et al.

(10) Patent No.: US 6,890,545 B2
(45) Date of Patent: May 10, 2005

(54) FUNGICIDE AND METHOD FOR PRODUCING THE SAME

(75) Inventors: Iichiroh Ohhira, Okayama (JP);
Shinsuke Kuwaki, Kurashiki (JP);
Masumi Takahata, Okayama (JP);
Yoshiyuki Murata, Okayama (JP);
Mikiro Tada, Okayama (JP)

(73) Assignee: Biobank Co., Ltd., Okayama (JP)

( * ) Notice: Subject to any disclaimer, the term of this patent is extended or adjusted under 35 U.S.C. 154(b) by 0 days.

(21) Appl. No.: 10/360,093

(22) Filed: Feb. 7, 2003

(65) Prior Publication Data

US 2003/0170218 A1 Sep. 11, 2003

(30) Foreign Application Priority Data

Feb. 13, 2002 (JP) .......................................... 2002-035906
Sep. 12, 2002 (JP) .......................................... 2002-267057

(51) Int. Cl.$^7$ .......................... A01N 25/00; A61K 31/19
(52) U.S. Cl. ....................................... 424/405; 514/557
(58) Field of Search ........................... 424/405; 514/572, 514/574, 557

(56) References Cited

U.S. PATENT DOCUMENTS 6,211,238 B1 * 4/2001 Castillo et al. ............. 514/563

FOREIGN PATENT DOCUMENTS

| JP | 9-97689 | 4/1993 |
|---|---|---|
| JP | 9-263539 | 7/1997 |
| JP | 9-263539 | * 10/1997 |
| JP | 2000-300284 | 10/2000 |

OTHER PUBLICATIONS

Kuwaki et al, Antifungal activity of the fermentation product of herbs by lactic acid bacteria against tinea, 2002, vol. 94 No. 5, pp. 401–405.*

Iichiro Ohhira et al., "Antimicrobial activity against methicillin–resistant *Staphylococcus aureus* in the culture broth of *Enterococcus faecelis* TH 10, an isolate from Malaysian fermentation food, Temph", *Japanese Journal of Dairy and Food Science*, vol. 45, No. 4, 1996.

Iichiro Ohhira et al., "Purification of Anti–*Escherichia coli* O–157 components produced by *Enterococcus faecalis* TH10, an isolate from Malaysian fermentation food, tempeh", *Milk Science*, vol. 49, No. 2, 2000.

* cited by examiner

*Primary Examiner*—Alton Pryor
(74) *Attorney, Agent, or Firm*—Koda & Androlia

(57) ABSTRACT

Provided is a fungicide against a filamentous fungus which contains a compound produced by a microorganism belonging to the genus *Enterococcus*. The fungicide wherein said microorganism is *Enterococcus faecalis* TH10 is preferable and the fungicide which is obtained by fermentation after inoculating said microorganism is preferable as well. A safe and useful fungicide against a filamentous fungus including a compound produced by a microorganism can be supplied and used beneficially as a dermatologic medicine, a pesticide and a soil amendment.

18 Claims, 1 Drawing Sheet

US 6,890,545 B2

FUNGICIDE AND METHOD FOR PRODUCING THE SAME

BACKGROUND OF THE INVENTION

1. Field of the Invention

The present invention relates to a fungicide against a filamentous fungus which contains a compound produced by a microorganism belonging to the genus *Enterococcus*, as well as a method for its production and its usage.

2. Description of the Related Art

With regard to antifungal activity of microorganisms belonging to the genus *Enterococcus* there have been some studies reported. For example, Japanese Patent Laid-Open No. 97689/1993 discloses an infection protective agent which contains cells of microorganisms which belong to the genus *Enterococcus* or their treated material as an active component. Japanese Patent Laid-Open No. 263539/1997 discloses a therapeutic agent for dermatopathy which comprises lactic acid bacteria and their treated substances as active ingredients. These documents disclose that the strain used particularly in the Examples is *Enterococcus faecalis* NF-1011 which can be used as a fungicide against fungi such as *Candida* etc. Said documents disclose a usage of not the product by bacteria but bacterial cells themselves, that is, ingestion of dead bacterial cells, living bacterial cells, or fungus bodies that are processed by grinding, extracting with water etc.

Japanese Patent Laid-Open No. 300284/2000 discloses that phenyllactic acid produced by using lactic acid bacterium, that is, *Enterococcus faecalis*, has antibacterial activity. It also discloses that said phenyllactic acid shows a strong antibacterial activity against harmful microorganisms such as enterohemorrhagic *E. coli* O-157, methicillin-resistant *Staphylococcus aureus* (MRSA), etc. Moreover, anti-MRSA activity of *Enterococcus faecalis* TH10 is disclosed in *Japanese Journal of Dairy and Food Science*, vol. 45, No. 4, A93–96 (1996) and anti-*E. coli* O-157 activity is disclosed in *Milk Science*, vol. 49, No. 2, 81–86 (2000).

Each of said documents discloses that *Enterococcus faecalis* has antibacterial activity. Although they disclose that said microorganism is effective against bacteria such as O-157, MRSA, etc., and that it is effective against *Candida*, a fungus categorized in yeast, they do not disclose that it is effective against fungi categorized in filamentous fungi.

Filamentous fungi, particularly dermatophytes, are causative fungi of many dermatological diseases represented as so-called tinea. Agent with effective antifungal activity against dermatophytes has been longed for. Dermatophytes are dermatologic filamentous fungi which usually infect keratine tissues such as keratinocyte, hair and nails of mammals, including human. Dermatophytes are classified into the following three genera: *Trichophyton*, *Microsporum*, and *Epidermophyton*. According to the Epidemiological Investigation Committee for Human Mycoses in the Japanese Society for Medical Mycology, the incidences of tinea is reported to account for almost 100% with two species such as *Trichophyton rubrum* (70.5%) and *Trichophyton mentagrophytes* (26.8%) followed by *Microsporum canis*, *Epidermophyton floccosum*, *Microsporum gypseum*, *Trichophyton glabrum* and *Trichophyton verucosum* in order.

In spite of a wide range of usage of clinically effective fungicides such as imidazole compounds or antibiotics, requirements to a novel and effective fungicide that is free of any side effects have yet been longed for at present. On treatment of tinea, it is a fact that many patients are reluctant to use a synthetic medicine in view of safety since they need to use it repeatedly for a long time in many cases.

Moreover, there are some filamentous fungi that inhibit the growth of useful plants. For example, *Rosellinia necatrix* and *Helicobasidium mompa* grow in land around the roots of fruit trees etc. and inhibit their growth. *Fusarium oxysporum* and *Pythium graminicola* cause seedling disease of rice or the phenomenon of turf which is blasted locally, and *Pyricularia oryzae* causes blast of rice.

Many kinds of effective fungicides as represented with synthetic chemical compounds against filamentous fungi that inhibit the growth of plants are known. However, these chemical compounds may pose the risk to give harmful influence to the human body as residue in crops. They may also pose the risk to pollute the surrounding environment such as land and rivers. Therefore, a safe fungicide without such problems has been sought for.

The object of the present invention is to solve the above problem and to provide a safe and effective fungicide against filamentous fungi.

SUMMARY OF THE INVENTION

The present invention is a fungicide against filamentous fungi that contains compounds produced by a microorganism belonging to the genus *Enterococcus*. In this fungicide, said microorganism being *Enterococcus faecalis* is preferable and being *Enterococcus faecalis* TH10 is most preferable. Preferably, said filamentous fungus is a dermatophyte. It is preferable that said filamentous fungus is one of the fungi selected from the group consisting of *Rosellinia necatrix*, *Helicobasidium mompa*, *Fusarium oxysporum*, *Pythium graminicola* and *Pyricularia oryzae* as well.

It is preferable that the fungicide of the present invention contains at least one of carboxylic acids selected from the group consisting of lactic acid, acetic acid, malonic acid and oxalic acid. It is also preferable that the pH is 6 or less. The fungicide of this invention can preferably be used as a dermatologic medicine, a pesticide and a soil amendment.

Further, the above object is achieved by providing a method for producing a fungicide against filamentous fungi wherein said fungicide is produced by a microorganism belonging to the genus *Enterococcus*. In this method, it is preferable that fermentation is carried out by inoculating a microorganism belonging to the genus *Enterococcus* into a starting material containing a carbon source and a nitrogen source.

DETAILED DESCRIPTION OF THE INVENTION

Figure 1:
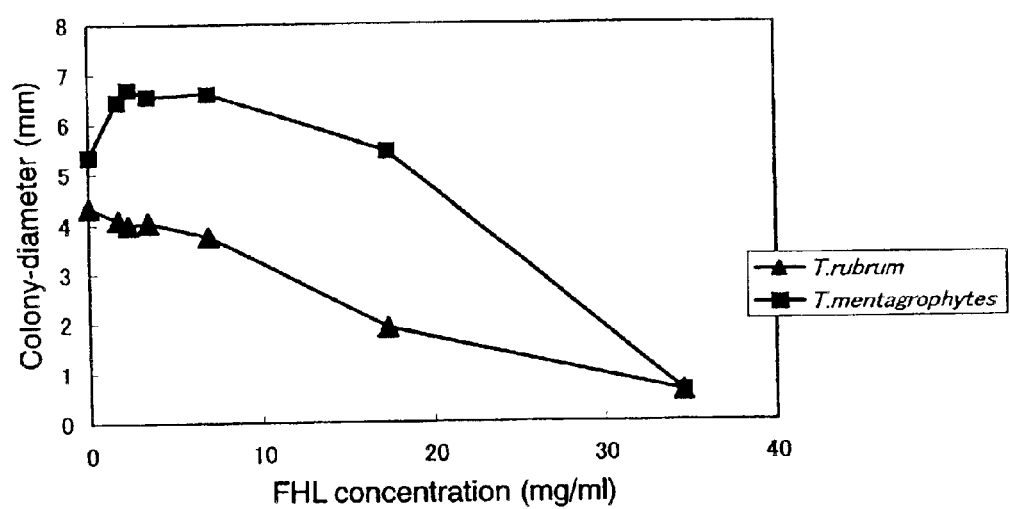
FIG. 1 shows the diameter of the colony against the concentration of FHL (fermentation product of herbs by lactic acid bacteria) obtained in Example 4.

The fungicide of the present invention is a fungicide which contains a compound produced by a microorganism belonging to the genus *Enterococcus*. On the present invention, the microorganism that was used to produce a compound with antifungal activity belongs to the genus *Enterococcus*. The inventors of the present invention found out that the compound produced by a microorganism belonging to this genus possesses antifungal activity against filamentous fungi.

Examples of microorganisms belonging to the genus *Enterococcus* include *Enterococcus faecalis, Enterococcus faecium*, etc. Among these, *Enterococcus faecalis* is preferable. It is also preferable that said microorganisms are lactic acid bacteria that produce lactic acid in cultivation or fermentation. In many cases, these microorganisms are safe bacteria without harmful influences even they live in human intestines etc., and the compound produced by them is also safe.

Among these, the most preferable strain to use in the present invention is *Enterococcus faecalis* TH10. Although *Enterococcus faecalis* TH10 corresponds to refusal for deposit in International Patent Organism Depositary, National Institute of Advanced Industrial Science and Technology, the inventors of the present invention will guarantee its distribution. *Enterococcus faecalis* TH10 is isolated from Malaysian fermented foods, tempeh (*Japanese Journal of Dairy and Food Science*, vol. 39, No. 4, A115–A121 (1990)) by the inventors of the present invention. Since it is a lactic acid bacterium which is contained in food, the safety of this strain to the human body is sufficient.

The bacteriological properties of *Enterococcus faecalis* TH10 are as follows:

| | |
|---|---|
| Gram's staining | + |
| Morphology | diplococcus, streptococcus |
| Oxygen requirement: | |
| Strict aerobes | − |
| Facultative anaerobes | + |
| Catalase activity | − |
| Properties shown in litmus milk: | |
| Reduction | + |
| Acid producing activity | + |
| Coagulation | + |
| Gelatin liquefying activity | + |
| Optical rotary power of produced lactic acid L- | (+) |
| Gas producing activity from glucose | − |
| Growth in 6.5% NaCl medium | + |
| Growth in pH9.6 | + |
| Resolution of arginine | + |
| Resolution of hippurate | + |
| Sugars fermentation: | |
| Cellobiose | + |
| Potassium gluconate | − |
| Glucose | + |
| Glycerol | − |
| Inulin | − |
| Lactose | + |
| Mannitol | ± |
| Raffinose | − |
| Ribose | + |
| Salicin | + |
| Sorbitol | − |
| Sorbose | − |
| Sucrose | ± |
| Trehalose | + |
| Salt-tolerance: | |
| 5% NaCl | + |
| 10% NaCl | ± |
| 15% NaCl | − |
| Heat-tolerance: | |
| 40° C. | + |
| 45° C. | ± |
| 50° C. | − |
| 55° C. | − |
| Acid-tolerance: | |
| pH 3.0 | − |
| pH 3.5 | ± |
| pH 4.0 | ± |
| pH 4.5 | + |
| Acidity (%): | |
| in 0% NaCl medium | 0.22 |
| (0% NaCl skim milk (as control) | 0.14) |
| in 5% NaCl medium | 0.24 |
| (5% NaCl skim milk (as control) | 0.16) |
| pH value: | |
| in 0% NaCl medium | 6.11 |
| in 5% NaCl medium | 5.94 |
| Proteolytic activity (Free tyrosine content; mg/5 ml): | |
| 0% NaCl medium, 38° C., 24 hr-cultivation | 1.32 |
| 5% NaCl medium, 38° C., 24 hr-cultivation | 0.04 |
| G + C content (mol %) | 38.6 |

The compounds produced by the above microorganisms possess effective antifungal activity against filamentous fungi. The filamentous fungi targeted on by the fungicide in this invention are not particularly limited. Examples of the filamentous fungi include *Trichophyton rubrum, Trichophyton mentagrophytes, Rosellinia necatrix, Helicobasidium mompa, Fusarium oxysporum, Pythium graminicola, Pyricularia oryzae*, etc.

*Trichophyton* is a causal fungus of a dermatological disease, tinea, which usually infects on keratin tissues as keratinocyte, hair and nails. The fungicide of this invention is effective against these dermatophytes such as *Trichophyton*. Dermatophytes are classified into three genera such as *Trichophyton, Microsporum* and *Epidermophyton*, and among those, it is effective against the genus *Trichophyton* with a specially high incidence of tinea. More concretely, it is particularly effective against *Trichophyton rubrum* and *Trichophyton mentagrophytes*.

Moreover, the fungicide of the present invention is effective against filamentous fungi that inhibit the growth of plants. Those filamentous fungi include *Rosellinia necatrix, Helicobasidium mompa, Fusarium oxysporum, Pythium graminicola* and *Pyricularia oryzae* as representatives.

The fungicide of this invention contains compounds produced by microorganisms belonging to the genus *Enterococcus*. The method to produce said compounds by the microorganisms is not particularly limited. It is sufficient once the compounds are obtained. While the microorganisms are cultivated with nutritious sources, the compounds are produced from bacterial cells of the microorganisms. The microorganisms may be cultivated in the medium prepared under sterilized conditions, or fermented under open conditions.

For the medium prepared for cultivation under sterilized conditions, expensive sterilized materials such as sugars, amino acids, etc. are used in many cases. Moreover, since medium preparation or cultivation also needs to be conducted under sterilized conditions, its cost for the facilities will expand if the cultivation is conducted for a long time. Therefore, it is preferable to have it fermented under open conditions with regard to these points.

The starting materials in case of fermentation is not particularly limited, but using natural products as starting materials will coincide with the needs of patients and will be beneficial with regard to the production cost. Specifically, it is preferable to have a method as to inoculate a microorganism belonging to the genus *Enterococcus* into a starting material containing a carbon source and a nitrogen source, more preferably carbohydrate and protein, and as to ferment it. As the natural materials containing carbohydrate and protein, particularly as plant materials, crops such as rice, wheat, corn, sugarcanes, beans, seeds, etc. can be used. Their processed products such as rice bran, rape cake, molasses, etc. can also be used.

Fermentation is started by inoculating a microorganism belonging to the genus *Enterococcus* into the above starting materials after appropriate amount of water is added. When fermentation aroma occurs during the process of fermentation, it may give unpleasant odor to the product. In such case, it is preferable to add aromatic plant (herbal) materials for adjustment of aroma. Such plant materials are not particularly limited as long as they contain aromatic elements. Preferable examples are lavender, lemon balm, mugwort etc. In one of the preferable embodiments, the fungicide of the present invention is used for the human body. In case it is applied on the skin, for example, quality of the aroma is very important for patients. Particularly for treatment of tinea, there are many cases that patients need to apply it for a long period. Therefore, if they are reluctant to smell the odor of the medicine, it will interfere the long repeated use. It is also preferable that loquat leaves, for example, are added into the starting materials, because loquat leaves are supposed to contain ingredients that would leave the skin softer, smoother, and healthier. However, in case of using the fungicide as a pesticide or a soil amendment etc., these aromatic plant materials and loquat leaves etc. are not particularly necessary.

The condition of fermentation is not particularly limited. It is fermented by inoculating a microorganism belonging to the genus *Enterococcus* into the starting materials prepared without sterilization. The fermentation temperature is preferably from 15 to 40° C. The fermentation time can be adjusted properly according to its usage and starting materials. It is usually one week or more, preferably one month or more, and more preferably, 3 months or more. During the fermentation, the fermentation will progress even under the conditions that other microorganisms which do not belong to the genus *Enterococcus* are mixed in. However, there are no particular problems as long as microorganisms which belong to the genus *Enterococcus* predominate.

The fungicide of the present invention is obtained from the above fermentation or cultivation, and the antifungal compounds contained in the fungicide are produced by microorganisms belonging to the genus *Enterococcus*. They are produced out of the bacterial cells during fermentation or cultivation. Therefore, it does not mean that the bacterial cells themselves are beneficial. To maintain the quality, it may be sterilized by heating etc. after the production of the antifungal compounds. Since unnecessary solid will disturb homogenization of quality, or it will disturb smooth application if used as a dermatologic medicine, it is preferable to remove insoluble substances by centrifugation or filtration. The bacterial cells may be removed at the same time.

The fungicide obtained as such is preferably to contain at least one of the carboxylic acids selected from the group consisting of lactic acid, acetic acid, malonic acid and oxalic acid. Since the fungicide contains these carboxylic acids, the pH of the fungicide becomes low, and antifungal activity of the fungicide is exhibited more effectively. The fungicide of the present invention obtained by lactic acid fermentation is preferable. It is more preferable to contain other carboxylic acids in addition to lactic acid at the same time. Moreover, with regard to antifungal activity, it is even more preferable to contain acetic acid or malonic acid. The preferable content of at least one of carboxylic acids selected from the group consisting of lactic acid, acetic acid, malonic acid and oxalic acid differs according to its usage, but usually, it is 1 mM (mmol/L) or more, preferably, 10 mM (mmol/L) or more in total.

Furthermore, it is preferable that the pH of the fungicide of the present invention is 6 or less. As shown in the following Examples, with regard to the fermented liquid which was neutralized with sodium bicarbonate to pH 6.65, antifungal activity of the fermented liquid decreased. With relation to the fact that the fungicide contained the carboxylic acids, it is suggested that some acid compounds would contribute to antifungal activity. More preferably, the pH of the fungicide is 5 or less. Moreover, with regard to its application on the skin, since too high acidity will be too stimulative to the skin, its pH is usually 1 or more, preferably, 2 or more, and more preferably, 3 or more.

The usage of the fungicide of the present invention is not particularly limited as long as it is used against filamentous fungi. It can be used as a medicine in order to treat diseases caused by filamentous fungi whose hosts are animal cells, or as a pesticide or a soil amendment to remove filamentous fungi (for example *Rosellinia necatrix* which grows on plant roots) whose hosts are plant cells.

Among all, one of the preferable embodiments is a dermatologic medicine against dermatologic diseases triggered by filamentous fungi such as tinea. As for a dermatologic medicine, the fermented liquid produced as above can be used as it is, but can be concentrated or diluted properly, or added to some other components. Those other components added are not particularly limited. Various kinds of bases such as oil or wax, aroma, vitamin, stabilizer, etc. can be blended.

A pesticide against filamentous fungi which infect plants, for example, a fungicide is also one of the preferable embodiments. In addition, a soil amendment which prevents harmful influence of such filamentous fungi is one of the preferable embodiments.

*Rosellinia necatrix* causes white root rot to grapes, pears, loquats etc. when these fruit trees are infected. *Helicobasidium mompa* causes purple root rot to peaches, apples etc. when these fruit trees are infected. These filamentous fungi grow around the roots of fruit trees etc. in land and inhibit the growth of the roots. Since the fungicide of the present invention is effective against these filamentous fungi, it is useful as a pesticide for fruit trees or as a soil amendment for land of orchard. On using it, a method to inject it into land around the fruit trees after diluted properly in case of necessity, and a method to apply directly to the root part are suggested.

*Fusarium oxysporum* infects mainly gramineous root and causes seedling disease of rice or fusarium patch of turf (the part blasted locally on a golf course etc.). *Pythium graminicola* also infects mainly gramineous root and causes seedling disease and root rot of rice, and pythium blight of turf (the part blasted locally on a golf course etc.). *Pyricularia oryzae* causes blast of rice. Therefore, the fungicide of the present invention is also useful as a pesticide for these gramineous plants. Concretely, it is useful as a fungicide or a soil amendment for rice and turf. For its use, it can be applied directly to the plants, or injected into land after diluted properly in case of necessity.

EXAMPLES

The invention is described in more detail with reference to the following Examples, which, however, are not intended to restrict the scope of the invention.

The fermented liquid used in Example 1 is available on the market by BIOBANK Co., Ltd. with its trade name as FHL (the fermentation product of herbs by lactic acid bacteria). It is produced as follows.

Starting materials for fermentation are molasses (Shoyu Kogyo Co., Ltd), rice bran (obtained from a rice mill), and rape cake (Kato Oil Mill Co., Ltd.) as major components, and loquat leaves, lavender, lemon balm and mugwort as minor components. Water was added to them, which were mixed. *Enterococcus faecalis* TH10 was inoculated into MRS broth (Oxoid Ltd.) and cultivated at 37° C. for 2 days to make a starter. The starter was seeded to the starting materials and mixed to start fermentation.

The mixed amounts of each starting material are shown in weight (g) per liter (L) as follows.

| | |
|---|---|
| Molasses | 400.0 g |
| Rice bran | 10.0 g |
| Rape cake | 10.0 g |
| Loquat leaves | 12.0 g |
| Lavender | 0.3 g |
| Lemon balm | 0.3 g |
| Mugwort | 0.7 g |
| Starter | 40.0 g |

Molasses, rice bran and rape cake are major components of the starting materials which supply microorganisms with carbohydrate, protein, and lipid. Particularly, molasses is useful to supply carbohydrate, while rice bran and rape cake are useful to supply protein. Lavender, lemon balm, and mugwort are added as minor components to adjust aroma of the fermented liquid. And, loquat leaves are added as a minor component to protect the skin.

Under open conditions, a three-month fermentation at room temperature was done. During that time, it was stirred twice a week. According to the observation through a microscope, although lactic acid bacteria other than *Enterococcus faecalis* TH10 existed in the fermented liquid, *Enterococcus faecalis* TH10 was predominant all the time within the fermentation period.

FHL was obtained by removing insoluble substances after filtrating the fermented liquid produced as above. Its pH was from 3.7 to 3.8.

Carboxylic acids contained in the above FHL were analyzed. The analysis of carboxylic acids was conducted by using a high performance liquid chromatography (HPLC) equipped with an octadecyl silica gel (ODS) column, and by measuring the absorbance at 214 nm with a UV detector. For mobile phase, a 10 mM (mmol/L) potassium dihydrogen phosphate solution adjusted its pH to 2.3 with phosphoric acid was used. Its flow rate was 0.7 mL/min. A sample was diluted 10-fold with mobile phase solution. And, it was measured by injecting 10 $\mu$L after filtrating with a 0.22 $\mu$m membrane filter. Each carboxylic acid was determined by comparing with the retention times of standard substances.

As a result of the above analysis, FHL was found to contain four major carboxylic acids. Those carboxylic acids were oxalic acid, malonic acid, lactic acid and acetic acid from the retention times of the obtained chromatogram. The concentrations of these carboxylic acids are 35.7 mM oxalic acid, 266 mM malonic acid, 296 mM lactic acid, and 300 mM acetic acid. These concentrations are the total concentrations of free carboxylic acids and carboxylic acids forming salts. The concentrations of the test medium in Example 1 are 1/10 of the concentrations of FHL. As will be explained later, while the pH of the test medium of Example 1 is 4.01, the pH of the medium with the same content of free carboxylic acids (Comparative Example 9) is 2.70. These acidities differed each other greatly. Therefore, it is suggested that the most part of carboxylic acids in FHL form salts.

The fungi used in the following Examples were obtained as below: *Trichophyton rubrum* was purchased from Chuo Medical Technology Corp. *Trichophyton mentagrophytes*; IFO No. 5466 was purchased from the Institute for Fermentation, Osaka. *Candida albicans*; IFO No. 1060 was also purchased from the Institute for Fermentation, Osaka. *Rosellinia necatrix* was distributed from Okayama Agricultural Experiment Station. *Helicohasidium mompa*; IFO No.31651, *Fusarium oxysporum*; IFO No. 32203, *Pythium graminicola*; IFO No. 32330, and *Pyicularia oryzae*; IFO No. 31175 were purchased from the Institute for Fermentation, Osaka.

Example 1

Antifungal activity of the sample was determined using the agar dilution method. Sabourand agar medium was prepared as a standard medium. The composition of the medium was as follows:

| | |
|---|---|
| Glucose | 40 g |
| Polypepton | 10 g |
| Agar | 15 g |
| Distilled water | 1000 mL |

FHL was autoclaved at 121° C. for 15 minutes. After centrifuging and removing the precipitate, the supernatant was obtained. Two mL of the obtained supernatant was placed in a sterilized petri dish, and 18 mL of the autoclaved standard medium was poured in it. Then, it was immediately shaken gently and left until the agar gelled to prepare the sample plate. The pH of the sample plate was 4.01.

Two kinds of *Trichophytons* (*Trichophyton rubrum* and *Trichophyton mentagrophytes*) mentioned above were inoculated separately on the standard plate. They were precultivated in an incubator at 28° C. for 10 days. Both *Trichophytons* which were precultivated as such were inoculated on the sample plates mixed with FHL. On inoculation, a 5 mm cork borer was sterilized with a flame. A colony in disk form was taken out from the perimeter portion of the white colony, and this colony disk was carefully placed into the center of the sample plate which was mixed with FHL. In this method, the colony disk was turned over and inoculated in the manner that the fungal filaments were in direct contact with the medium. The colony-diameter was measured after cultivation at 28° C. for 12 days. The results are summarized in Table 1. In the table, the value of antifungal activity (%) is calculated from the following equation.

Antifungal activity $(\%) = 100 - [(x-5)/(y-5)] \times 100$

In the equation, "x" refers to the value of the colony-diameter (mm) after cultivation on the sample plate; "y" refers to the colony-diameter (mm) after cultivation on the standard plate; and "5" (mm) refers to the value equivalent to the diameter of the colony disk cut off with a cork borer.

Example 2

Instead of using intact FHL in Example 1, FHL which was neutralized with sodium bicarbonate was used. And, it was autoclaved as Example 1. After centrifugation, the precipitate was removed, then the supernatant was obtained as Example 1. Using this supernatant, two kinds of *Trichophytons* were inoculated and cultivated on the sample plate prepared as Example 1. The pH of the sample plate was 6.65. The experimental results are shown in Table 1.

Example 3

Two kinds of *Trichophytons* were inoculated on the sample plate and cultivated as Example 1 using the following supernatant instead of using FHL in Example 1. *Enterococcus faecalis* TH10 was inoculated into MRS broth, which was cultivated at 37° C. for 2 days. The insoluble substance including the bacterial cells was centrifuged. The supernatant (TH10-broth) was obtained by removing the insoluble substance. The pH of TH10-broth was 4.7. The sample plate was prepared as Example 1. The pH of the sample plate was 4.92. The results are summarized in Table 1.

Comparative Example 1

Two kinds of *Trichophytons* were inoculated and cultivated as Example 1 using the following plate instead of the sample plate prepared in Example 1. The sample plate which was used here was prepared only with 20 mL of the autoclaved standard medium (Sabourand agar medium). The results are summarized in Table 1.

Comparative Example 2

Two kinds of *Trichophytons* were inoculated and cultivated as Example 1 using the following plate instead of the sample plate prepared in Example 1. One M hydrochloric acid was added to 50 mM potassium hydrogen phthalate buffer, and the pH was adjusted (pH1.50). And the buffer was filtered with a 0.22 μm membrane filter. Then, 2 mL of the buffer was mixed with 18 mL of the standard medium and the sample plate was prepared. The pH of the sample plate was 3.80. The results are summarized in Table 1.

Comparative Example 3

Two kinds of *Trichophytons* were inoculated and cultivated as Example 1 using the following plate instead of the sample plate prepared in Example 1. One hundred mM citric acid—NaOH buffer (pH 3.65) was filtered with a 0.22 μm membrane filter. Two mL of the buffer was mixed with 18 mL of the standard medium, and the sample plate was prepared. The pH of the sample plate was 4.05. The results are summarized in Table 1.

Comparative Example 4

Two kinds of *Trichophytons* were inoculated and cultivated as Example 1 using the following plate instead of the sample plate prepared in Example 1. F-GEN, a medicine for treatment of athlete's foot from Daigen Medical Co., Ltd., was filtered with a 0.22 μm membrane filter. Two mL of F-GEN was mixed with 18 mL of the standard medium, and the sample plate was prepared. F-GEN, a medicine for treatment of athlete's foot, is liniment containing 3.0 g of undecylenic acid and 4.0 g of salicylic acid as effective components in 100 mL. The results are summarized in Table 1.

TABLE 1

| Sample plate | T. rubrum | | T. mentagrophytes | |
|---|---|---|---|---|
| | Diameter of the colony (mm) | Antifungal activity (%) | Diameter of the colony (mm) | Antifungal activity (%) |
| Example 1: FHL | 6.1 ± 0.1 | 97 | 6.5 ± 0.7 | 97 |
| Example 2: Neutralized FHL | 23.5 ± 0.7 | 52 | 42.0 ± 7.1 | 24 |
| Example 3: TH10 Broth | 42.1 ± 0.1 | 4 | 48.0 ± 9.9 | 13 |
| Comp. Ex. 1: Standard medium | 43.5 ± 2.1 | 0 | 54.3 ± 2.9 | 0 |
| Comp. Ex. 2: Phthalate buffer | 21.0 ± 1.5 | 58 | 51.1 ± 2.4 | 6 |
| Comp. Ex. 3: Citrate buffer | 26.5 ± 1.5 | 44 | 14.8 ± 0.7 | 80 |
| Comp. Ex. 4: F-GEN | 6.1 ± 0.1 | 97 | 5.5 ± 0.7 | 99 |

As shown in the experimental results above, in Example 1 using the fermented liquid of *Enterococcus faecalis* TH10, a distinct antifungal activity was found in comparison with Comparative Example 1 using the standard medium. In comparison with Comparative Example 4 using F-GEN, a medicine for treatment of athlete's foot containing carboxylic acids as effective ingredients which is available on the market, it was also found that almost the same level of antifungal activity was obtained. Meanwhile, in Example 2 in which said fermented liquid (FHL) was neutralized, the antifungal activity decreased partially in comparison with Example 1. Therefore, it is found that using FHL under acidic condition is more effective. Moreover, in Example 3 using the supernatant cultivated with *Enterococcus faecalis* TH10 for a short time, its effect was not found sufficient. Thus, for production of antifungal compounds, a long term fermentation was found to be effective. As shown in Comparative Example 2 and 3, with only the adjustment of pH of the buffers of phthalate and citrate, antifungal activity of the buffers was not sufficient in comparison with Example 1. It is suggested that said fermented liquid (FHL) has antifungal activity not only by being acidic but also by containing unique antifungal compounds. Since antifungal activity of FHL decreases by neutralization, it is assumed that unique antifungal compounds would have acidic groups.

Example 4

After autoclaving FHL at 121° C. for 15 minutes, it was diluted with various amount of sterilized water. Then, 2 mL of diluted FHL was mixed with 18 mL of the standard medium. The sample plates of each concentration from 1/200 (solid content 1.73 mg/mL) to 1/10 (solid content 34.6 mg/mL) were prepared as Example 1. And, 1/10 was as the same concentration as Example 1 which was not diluted with sterilized water. The solid content of FHL was measured by freeze-drying and it was 34.6 weight %. Using the sample plates of each concentration, two kinds of *Trichophytons* were inoculated and cultivated as Example 1. The results are shown in FIG. 1.

As shown in FIG. 1, in case of the plate containing 34.6 mg/mL (equivalent to Example 1:10-fold dilution) of solid in FHL, antifungal activities were sufficiently shown for both *Trichophyton rubrum* and *Trichophyton mentagrophytes*. In the plate containing 17.3 mg/mL of FHL, about 50% of antifungal activity was shown against *Trichophyton rubrum* but no significant activity was shown against *Tri-* chophyton mentagrophytes. In the concentration of 6.92 mg/mL or below, no significant activity against both *Trichophytons* was shown.

Example 5

The colony prepared by inoculation and cultivation of two kinds of *Trichophytons* in Example 1 was transferred to the standard plate, and it was cultivated at 28° C. for 12 days. As a result, since the growths of the colonies were not observed, it was found that antifungal activity of FHL was not fungistatic, but fungicidal.

Comparative Examples 5 to 9

Two kinds of *Trichophytons* were inoculated and cultivated as Example 1 using the following plate instead of the sample plate prepared in Example 1. Two mL of the following solutions filtered with a 0.22 μm membrane filter were mixed with 18 mL of the standard medium, and the sample plates were prepared. The results are summarized in Table 2.

Comparative Example 5: 36 mM oxalic acid
Comparative Example 6: 300 mM malonic acid
Comparative Example 7: 300 mM lactic acid
Comparative Examole 8: 300 mM acetic acid
Comparative Example 9: 36 mM oxalic acid +300 mM maonic acid +300mM lactic acid +300 mM acetic acid

TABLE 2

| Sample plate | PH of the Medium | T. rubrum Diameter of the colony (mm) | Antifungal activity (%) | T. mentagrophytes Diameter of the colony (mm) | Antifungal activity (%) |
|---|---|---|---|---|---|
| Example 1: FHL | 4.01 | 6.1 ± 0.1 | 97 | 6.5 ± 0.7 | 97 |
| Comp. Ex. 1: Standard medium | 6.59 | 43.5 ± 2.1 | 0 | 54.3 ± 2.9 | 0 |
| Comp. Ex. 5: 3.6 mM Oxalic acid | 4.30 | 36.5 ± 1.1 | 18 | 17.6 ± 0.1 | 74 |
| Comp. Ex. 6: 30 mM Malonic acid | 2.91 | 5.5 ± 0.0 | 99 | 5.5 ± 0.0 | 99 |
| Comp. Ex. 7: 30 mM Lactic acid | 3.46 | 18.0 ± 5.0 | 66 | 17.7 ± 1.4 | 74 |
| Comp. Ex. 8: 30 mM Acetic acid | 4.12 | 5.4 ± 0.3 | 99 | 5.7 ± 0.3 | 99 |
| Comp. Ex. 9: Carboxylic acid mixture[1] | 2.70 | 5.6 ± 0.1 | 98 | 6.0 ± 0.0 | 98 |

[1] 3.6 mM oxalic acid + 30 mM malonic acid + 30 mM lactic acid + 30 mM acetic acid As shown in Table 2, antifungal activity was found in carboxylic acids, particularly in malonic acid and acetic acid. These suggest that a contribution of such carboxylic acids is one of the reasons for the expression of antifungal activity of this invention. Although the sample plate of Comparative Example 9 contains almost the same mole amount of free carboxylic acids to the mole amount of carboxylic acids contained in the sample plate of Example 1, its pH (2.70) is greatly lower than the pH (4.01) of Example 1. Therefore, in Example 1, many of the carboxylic acid roots form salts, and it is estimated that the amount of free carboxylic acids is much less than the amount of free carboxylic acids in Comparative Example 9.

Example 6

One M of hydrochloric acid was added to FHL which was used in Example 1. After FHL was adjusted to pH 3.5, pepsin was added to make the concentration of 1 mg/mL and treated at 35° C. for 1.5 hours. Next, FHL treated with pepsin was autoclaved at 121° C. for 15 minutes. The precipitate was removed after centrifugation and the supernatant was obtained. Two kinds of *Trichophytons* were inoculated and cultivated as Example 1 except that 2 mL of the supernatant was mixed with 18 mL of the standard medium. The results are summarized in Table 3.

Example 7

Two kinds of *Trichophytons* were inoculated and cultivated as Example 6 using trypsin instead of using pepsin as enzyme in Example 6. The results are summarized in Table 3.

TABLE 3

| Sample plate | T. rubrum Diameter of the colony (mm) | Antifungal activity (%) | T. mentagrophytes Diameter of the colony (mm) | Antifungal activity (%) |
|---|---|---|---|---|
| Example 1: FHL | 6.1 ± 0.1 | 97 | 6.5 ± 0.7 | 97 |
| Example 6: Pepsin treated | 5.7 ± 0.1 | 98 | 27.7 ± 3.5 | 54 |
| Example 7: Trypsin treated | 5.8 ± 0.2 | 98 | 13.6 ± 4.7 | 83 |
| Comp. Ex. 1: Standard medium | 43.5 ± 2.1 | 0 | 54.3 ± 2.9 | 0 |

As shown in Table 3, antifungal activities against *Trichophyton rubrum* similar to Example 1 were observed in Examples 6 and 7. However, against *Trichophyton mentagrophytes*, antifungal activity decreased in the case which was treated with protease as either pepsin or trypsin. These suggest that the fungicide of the present invention (FHL) contains polypeptide (protein or oligopeptide) which is hydrolysable when it is treated with protease, and that the polypeptide shows antifungal activity. Thus, it is assumed that carboxylic acids and polypeptide which are contained in the fungicide of this invention (FHL) show antifungal activity against filamentous fungi in a synergistic effect.

Comparative Example 10

Antifungal activity against *Candida albicans*, which is a yeast, was evaluated with FHL which was used in Example 1 instead of *Trichophytons* which belong to filamentous fungi. As for the standard medium, YM medium was prepared. The composition of the medium is as follows. And its pH was 5.6.

| | |
|---|---|
| Glucose | 10 g/L |
| Peptone | 5 g/L |
| Yeast extract | 3 g/L |
| Malt extract | 3 g/L |
| Agar | 15 g/L |

FHL was autoclaved at 121° C. for 15 minutes. The precipitate was removed by centrifugation and the supernatant was obtained. Two mL of the obtained supernatant was placed in a sterilized petri dish. Then, 18 mL of the standard medium which was autoclaved was poured, immediately shaken gently and left until the agar gelled to prepare the sample plate. The pH of the sample plate was 4.05.

*Candida albicans* was inoculated in a standard plate beforehand and precultivated in an incubator at 28° C. for 10 days. The *Candida albicans* precultivated as such was inoculated to the sample plate mixed with FHL. On inoculation, a colony was taken out from the precultivated medium with a platinum loop and diluted with 9 mL of physiological salt solution. After shaken well, it was applied on the sample plate and standard plate with a sterilized cotton swab and cultivated at 24° C. for 24 hours. On observation after cultivation, the colony on the sample plate showed the equivalent growth to the colony on the standard plate. As a result, it was found that FHL does not show any antifungal activity against *Candida albicans* at all.

Example 8

In this example, a fermented liquid (FL) which was fermented with the same procedure as FHL used in Example 1 was used. Loquat leaves, lavender, lemon balm, and mugwort were not used as the starting materials here. Because, since the filamentous fungus aimed in this example infects plant and is used for a pesticide and a soil amendment, the above starting materials are not necessary.

Antifungal activity of the sample was examined using the agar dilution method. Potato dextrose agar medium was used as the standard medium. Said medium was prepared by dissolving 15 g of the agar into Potato dextrose broth (Difco). The composition of the medium (content in a liter) is as follows.

| | |
|---|---|
| Potato infusion | 200 g |
| D-glucose | 20 g |
| Agar | 15 g |

FL was autoclaved at 121° C. for 15 minutes. The precipitate was removed by centrifugation and the supernatant was obtained. Two mL of the obtained supernatant was placed in a sterilized petri dish and 18 mL of the standard medium which was autoclaved was poured. Then it was immediately shaken gently and left until the agar gelled to prepare a sample plate. The pH of the sample plate was 3.89.

Five kinds of filamentous fungi such as *Rosellinia necatrix*, *Helicobasidium mompa*, *Fusarium oxysporum*, *Pythium graminicola* and *Pyricularia oryzae* were used and cultivated with the same procedure as Example 1 instead of using 2 kinds of *Trichophytons*. The results are summarized in Table 4.

Example 9

Instead of FL used in Example 8, neutralized sample prepared by adding sodium bicarbonate to FL was used. After autoclaving this as Example 8, the precipitate was removed by centrifugation and the supernatant was obtained. Then, five kinds of filamentous fungi were inoculated and cultivated using this supernatant as Example 8. The pH of the sample plate was 7.82. The results are summarized in Table 4.

Comparative Example 11

Five kinds of filamentous fungi were inoculated and cultivated as Example 8 by using the following plate instead of the sample plate prepared in Example 8. The plate consisted of 20 mL of the standard medium (Potato dextrose agar) which was autoclaved. The results are summarized in Table 4.

Comparative Example 12

Four kinds of filamentous fungi were inoculated and cultivated except for *Pyricularia oryzae* as Example 8 using the following plate instead of the sample plate prepared in Example 8. Fifty mM potassium hydrogen phthalate buffer (pH 4.01) was filtered with a 0.22 µm membrane filter, and 2 mL of the filtered buffer was mixed with 18 mL of the standard medium. The results are summarized in Table 4.

Comparative Example 13

Five kinds of filamentous fungi were inoculated and cultivated as Example 8 using the following plate instead of the sample plate prepared in Example 8. Tachigare-Ace (Sankyo Co., Ltd.) was diluted 50-fold, and 2 mL of diluted Tachigare-Ace was mixed with 18 mL of the standard medium. Tachigare-Ace is a liquid containing 30.0% of hydroxyisoxazole (3-hydroxy-5-methylisoxazole), and 4.0% of metalaxyl (methyl N-(2-methoxyacetyl)-N-(2,6-xylyl)-DL-alaninate. Tachigare-Ace is used as a growth promoter or fungicide for rice. It is assumed to be effective against seedling disease which is caused by *Pythium* and *Fusarium*. The results are summarized in Table 4.

Comparative Example 14

Two kinds of filamentous fungi (*Rosellinia necatrix* and *Pyricularia oryzae*) were inoculated and cultivated as Example 8 using the following plate instead of the sample plate prepared in Example 8. Frowncide (Ishihara Sangyo Kaisha, Ltd.) was diluted 100-fold, and 2 mL of diluted Frowncide was mixed with 18 mL of the standard medium. Frowncide is wettable powder containing 50.0% of fluazinam (3-chloro-N-(3-chloro-5-trifluoromethyl-2-pyridyl)-α, α,α-trifluoro-2, 6-dinitro-p-toluidine) as an effective ingredient. Frowncide shows fungicidal effect against filamentous fungi on a variety of agricultural products such as fruit trees and others. The results are summarized in Table 4.

TABLE 4

| | | *Rosellinia necatrix* | | *Helicobasidium mompa* | | *Fusarium oxysporum* | | *Pythium graminicola* | | *Pyricularia oryzae* | |
|---|---|---|---|---|---|---|---|---|---|---|---|
| | Sample plate | Diameter of the colony (mm) | Antifungal activity (%) | Diameter of the colony (mm) | Antifungal activity (%) | Diameter of the colony (mm) | Antifungal activity (%) | Diameter of the colony (mm) | Antifungal activity (%) | Diameter of the colony (mm) | Antifungal activity (%) |
| Example 8 | FL | 6.1 ± 0.3 | 98 | 6.7 ± 0.4 | 97 | 23.2 ± 5.2 | 65 | 6.8 ± 0.4 | 97 | 6.0 ± 0.3 | 97 |
| Example 9 | N-FL | 42.4 ± 0.2 | 45 | 12.2 ± 7.6 | 88 | 71.4 ± 4.5 | 0 | 80.7 ± 6.5 | 0 | 37.7 ± 1.5 | 0 |
| Comparative Example 11 | Standard Medium | 73.6 ± 8.0 | 0 | 62.8 ± 2.0 | 0 | 57.1 ± 3.0 | 0 | 74.8 ± 8.9 | 0 | 34.2 ± 1.7 | 0 |

TABLE 4-continued

|  | Sample plate | Rosellinia necatrix | | Helicobasidium mompa | | Fusarium oxysporum | | Pythium graminicola | | Pyricularia oryzae | |
| --- | --- | --- | --- | --- | --- | --- | --- | --- | --- | --- | --- |
|  |  | Diameter of the colony (mm) | Antifungal activity (%) | Diameter of the colony (mm) | Antifungal activity (%) | Diameter of the colony (mm) | Antifungal activity (%) | Diameter of the colony (mm) | Antifungal activity (%) | Diameter of the colony (mm) | Antifungal activity (%) |
| Comparative Example 12 | Phthalate buffer | 70.3 ± 0.0 | 5 | 8.1 ± 0.7 | 95 | 54.1 ± 4.1 | 5 | 13.1 ± 0.6 | 88 |  |  |
| Comparative Example 13 | Tachigare-Ace | 5.9 ± 0.3 | 99 | 6.5 ± 0.6 | 97 | 6.3 ± 0.6 | 98 | 6.3 ± 0.1 | 98 | 6.2 ± 0.5 | 96 |
| Comparative Example 14 | Frowncide | 6.6 ± 0.2 | 98 |  |  |  |  |  |  | 8.9 ± 1.7 | 87 |

As shown in Table 4, in Example 8 in which a fermented liquid (FL) was used, a clear antifungal activity was found compared with Comparative Example 11 using the standard plate. Except for a less efficacy against *Fusarium oxysporum* to a certain degree, it was found that almost the same degree of antifungal activity can be obtained compared with Comparative Example 13 and 14 using Tachigare-Ace and Frowncide, which are available pesticides on the market. Meanwhile, in Example 9 where FL was neutralized, antifungal activities of FL against *Rosellinia necatrix* and *Helicobasidium mompa* were partially decreased and antifungal activities against *Fusarium oxysporum*, *Pythium graminicola* and *Pyricularia oryzae* were lost compared with Example 8. Therefore, antifungal activities of FL against the above five genera, that is, *Rosellinia*, *Heicobasidium*, *Fusarium*, *Pythium* and *Pyricularia* were found more effective when FL was kept in acidic condition. As shown in Comparative Example 12, antifungal activity (especially against *Rosellinia necatrix* and *Fusarium oxysporum*) of the sample comprising phthalate buffer adjusted its pH to the same value as in Example 1 is not sufficient compared with Example 1.

As described in detail hereinabove with reference to its preferred embodiments, the fungicide of the present invention is produced by microorganisms. And, antifungal activity of the fungicide of the present invention can be the same as that of the available fungicides on the market. The fungicide of the present invention is a fungicide with safety and efficacy because it can be produced by lactic acid fermentation with natural materials from plants.

While the invention has been described in detail and with reference to specific embodiments thereof, it will be apparent to one skilled in the art that various changes and modifications can be made therein without departing from the spirit and scope thereof.

What is claimed is:

1. A method for producing an fungicide against a filamentous fungus wherein said fungicide is produced by a microorganism belonging to the *faecalis* TH10 wherein fermentation is carried out by inoculating a microorganism belonging to the *Enterococcus* into a starting material containing a carbon source and a nitrogen source.

2. The method for producing the fungicide according to claim 1, wherein the fermentation temperature is from 15 to 40° C. and the fermentation time is at least one week.

3. The method for producing the fungicide according to claim 2, wherein the fermentation time is at least one month.

4. The method for producing the fungicide according to claim 3, wherein the fermentation time is at least 3 months.

5. The method for producing a fungicide according to claim 1, wherein the fungicide contains at least one carboxylic acid selected from the group consisting of lactic acid, acetic acid, malonic acid and oxalic acid.

6. The method for producing a fungicide according to claim 5, wherein the content of the carboxylic acid is at least 1 mmol/L in total.

7. The method for producing a fungicide according to claim 5, wherein the pH of the fungicide is less than or equal to 6.

8. The method for producing a fungicide according to claim 7, wherein the pH of the fungicide is from 1 to 6.

9. A method for producing a fungicide against a filamentous fungus, wherein the fungicide is produced by a microorganism belonging to the genus *Enterococcus*, and the fungicide contains at least one carboxylic acid selected from the group consisting of lactic acid, acetic acid, malonic acid and oxalic acid.

10. The method for producing a fungicide according to claim 9, wherein the content of the carboxylic acid is at least 1 mmol/L in total.

11. The method for producing a fungicide according to claim 10, wherein the content of the carboxylic acid is at least 10 mmol/L in total.

12. The method for producing a fungicide according to claim 9, wherein the pH of the fungicide is less than or equal to 6.

13. The method for producing a fungicide according to claim 12, wherein the pH of the fungicide is less than or equal to 5.

14. The method for producing a fungicide according to claim 12, wherein the pH of the fungicide is from 1 to 6.

15. The method for producing a fungicide according to claim 14, wherein the pH of the fungicide is at least 2 or more.

16. The method for producing a fungicide according to claim 15, wherein the pH of the fungicide is at least 3 or more.

17. The method ibr producing a fungicide according to claim 9, wherein the fungicide is produced by *Enterococcus faecalis* TH10.

18. A method for producing a fungicide against a filamentous fungus, wherein the fungicide is produced by *Enterococcus faecalis* TH10.

* * * * *